United States Patent
Baerts

Patent Number: 5,156,799
Date of Patent: Oct. 20, 1992

[54] SAMPLING DEVICE FOR MOLTEN METAL

[75] Inventor: Christiaan Baerts, Beringen-Paal, Belgium

[73] Assignee: Electro-Nite International N.V., Antwerp, Belgium

[21] Appl. No.: 670,855

[22] Filed: Mar. 18, 1991

[30] Foreign Application Priority Data

Mar. 22, 1990 [DE] Fed. Rep. of Germany ....... 4009167

[51] Int. Cl.$^5$ ................................................. C21B 7/24
[52] U.S. Cl. .................................. 266/79; 73/864.56; 73/DIG. 9
[58] Field of Search .......... 266/79; 73/864.56, DIG. 9

[56] References Cited

U.S. PATENT DOCUMENTS

| | | |
|---|---|---|
| 3,685,359 | 8/1972 | Boron et al. |
| 3,915,002 | 10/1975 | Hance et al. |
| 4,037,478 | 7/1977 | Cure ............................... 73/425.4 R |
| 4,102,197 | 7/1978 | Bardenheuer |
| 4,401,389 | 8/1983 | Theuwis ............................ 374/140 |
| 4,535,640 | 8/1985 | Falk ................................ 73/864.55 |

FOREIGN PATENT DOCUMENTS

| | | |
|---|---|---|
| 871391 | 4/1979 | Belgium |
| 128665 | 12/1984 | European Pat. Off. .............. 266/79 |
| 0107219 | 12/1986 | European Pat. Off. |
| 2558092 | 6/1977 | Fed. Rep. of Germany |
| 3539973 | 5/1987 | Fed. Rep. of Germany |
| 3540228 | 5/1987 | Fed. Rep. of Germany |
| 8910869 | 12/1989 | Fed. Rep. of Germany |
| 2555745 | 5/1985 | France |
| 2560993 | 9/1985 | France |
| 2616540 | 12/1988 | France ............................. 73/DIG. 9 |
| 1239547 | 7/1971 | United Kingdom |

*Primary Examiner*—Melvyn J. Andrews
*Attorney, Agent, or Firm*—Panitch Schwarze Jacobs & Nadel

[57] ABSTRACT

Sampling devices for molten metal are known that consist of at least two cup-shaped, metallic components, which are arranged in such a way that their front (mating) surfaces face each other. These components form a sampling chamber, and they have an inlet pipe extending into the chamber. In order to construct a sampling device in a way that makes it quick and easy to remove the sample after the fluid metal has solidified, the chamber is coated with a wear-resistant layer which is temperature-stable up to approximately 1700° C. This layer should be applied at least in the area of the orifice and the wall area opposite the orifice. The front surfaces of the cup-shaped components can remain uncoated.

16 Claims, 3 Drawing Sheets

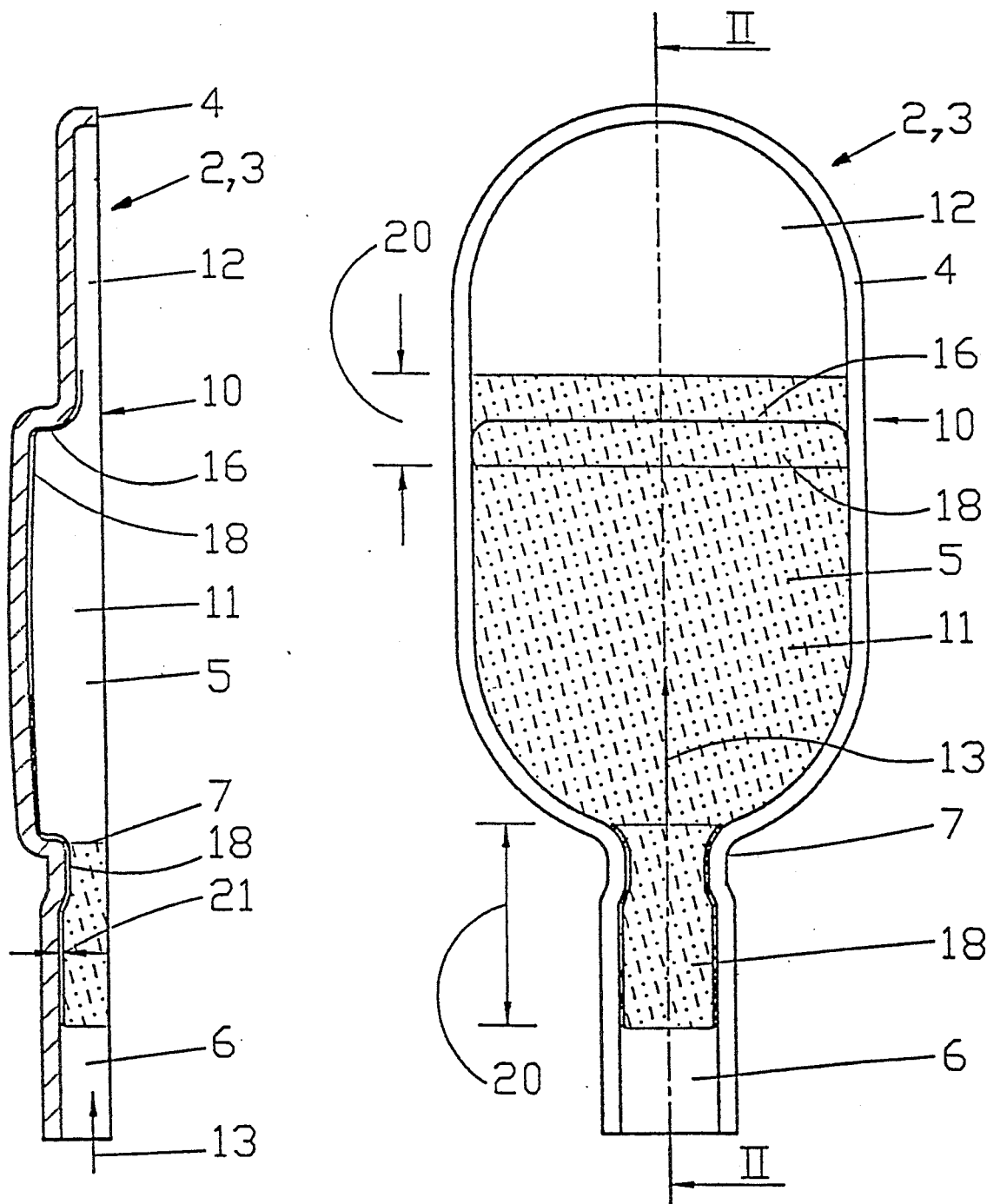

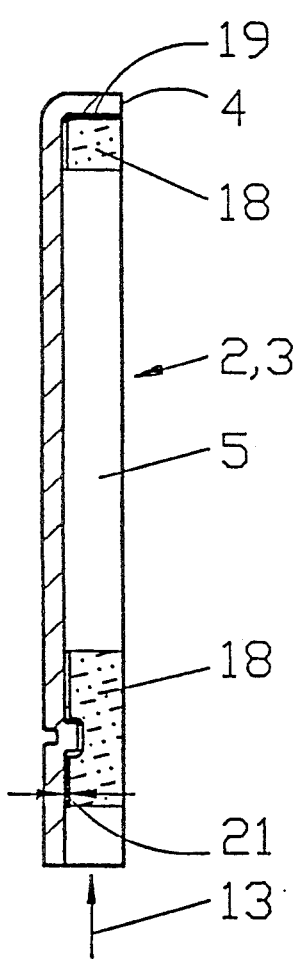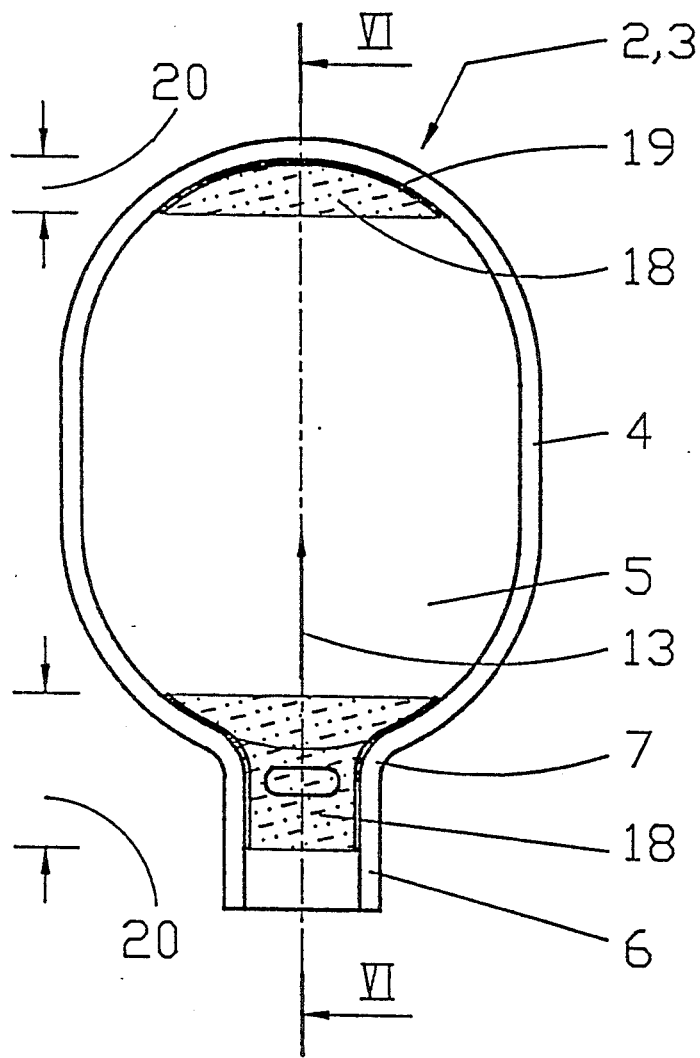
Fig.6
Fig.5

SAMPLING DEVICE FOR MOLTEN METAL

FIELD OF THE INVENTION

The present invention concerns a sampling device for molten metal with at least two cup-shaped, metallic components that are arranged in such a way; that their front (mating) surfaces face each other, whereby the metallic components form a sampling chamber having an inlet pipe opening into the chamber.

BACKGROUND OF THE INVENTION

Sampling devices of this type are known, for example, from Belgian Patent No. 871,391 or German Offenlegungschrift 35 40 228. These sampling devices can be part of a measuring head, with which measurements in molten metal can then be carried out or a sample withdrawn from the molten metal. The sampling device consists of two identical halves or half cups that enclose a hollow space or chamber. The two components of the sampling device are held together with a spring clip. An inlet pipe for the fluid metal opens into the chamber at its front end.

The measuring head with the sampling device is located on the end of a measuring lance. After the measuring lance is withdrawn from the molten metal to be analyzed, the sampling device can be removed from the measuring head. The solidified sample of molten metal is then located in the sampling device. The sample can ultimately be taken out by breaking open the sampling device in the area of the two cup-shaped metallic components that surround the chamber. The conventional chambers are formed in a way that yield flat, disk-shaped metallic samples. In some cases, the chamber of the sampling device can be subdivided into two chambers, whereby the chamber farther away from the inlet pipe usually has a substantially smaller thickness than the closer lying chamber. A sample is thereby produced with a thicker area and a thinner area, both of which can be drawn on in analyzing the metal.

The metallic components are galvanized with zinc so that they will not corrode while in storage.

It appears that breaking open the two cup-shaped, metallic components is problematical, since the fluid metal adheres to the components when it solidifies. This adherence can be so strong that the components must be mechanically removed, which can be very expensive. Even when the components are separable from one another by great force it has been observed that portions of the components still adhere to the metallic sample, thereby contaminating it. Since the components are galvanized with zinc, the sample is contaminated by this zinc or tends to form pores, so that the subsequent analysis of the sample yields an adulterated result. In addition, the mechanical force on the sample when the components are broken open can influence the structure of the metallic sample, if the components adhere to the sample, and the metallic sample can bend so that there is no longer a level work surface on the sample for subsequently removing any portion of the sample.

SUMMARY OF THE INVENTION

The purpose of the present invention is to construct a sampling device of the foregoing type in such a way that the sample can be quickly and easily removed, i.e. the metallic components of the sampling device can be easily taken apart after the fluid metal has solidified.

According to the invention, this purpose is achieved by the chamber, at least in the area of the orifice and the wall area opposite the orifice, being coated with a wear-resistant layer temperature-stable up to approximately 1700° C., and the front (mating) surfaces of the cup-shaped components remaining uncoated. Wear-resistant means that this layer remains connected to the metallic components during storage as well as during influx of the fluid metal. Temperature-stable up to approximately 1700° C. means that the layer will not be undermined upon contact with the fluid metal (e.g. steel) or exhibit substantial chemical or physical changes. Since the area of the orifice as well as the wall area opposite the orifice is coated with the wear-resistant layer, then precisely those areas of the sample chamber are coated upon which the very hot, fluid metal strikes as it streams into the sample chamber.

In an uncoated sampling device precisely these areas exhibit the tendency for the fluid metal to adhere to the sampling device upon solidification. Leaving the front surfaces of the cup-shaped, metallic components uncoated provides an exact alignment of the components. In addition, because of this, the fluid metal cools off more quickly, preventing the formation of a grade between the front surfaces, between which fluid metal would otherwise flow. Since only those areas of the sampling chamber considered to be critical are coated, the material necessary for the wear-resistant layer is kept to a minimum. The areas not to be coated can be covered with an appropriate mask when the wear-resistant layer is applied.

A wear-resistant layer with a thickness from 5 to 200 micrometers, preferably from 30 to 100 micrometers, has proven to be sufficient. Especially good results regarding the non-adherence of the wear-resistant layer and consequently the quality of the solidified sample surface are achieved when the wear-resistant surface has a thickness of approximately 60 micrometers. The thickness of the layer can vary in the range of about plus or minus 10 micrometers.

The coated parts of the sampling device should extend, at least in the area of the orifice, into the inlet pipe up to approximately half of its length and should coat the area of the walls of the sample chamber up to approximately 5 mm within the sampling chamber.

In some sampling devices the chamber formed by the cup-shaped, metallic components is subdivided into at least two areas of varying thicknesses, whereby, viewed from the direction of the inlet pipe, these chambers lie one behind the other and each one is separated from the other by means of a gradation that forms a strike surface. In these instances, the wear-resistant layer should be applied to this strike surface. This strike surface forms the wall surface lying directly opposite the inlet pipe, upon which surface the fluid metal streaming into the sample chamber strikes. Under certain circumstances, for such a sampling device subdivided into several partial chambers, it is superfluous to coat the wall of the sample chamber which lies most distant from the inlet pipe as seen in the direction of the inflowing metal. The reason for this is that the metal entering there creates a gas cushion which prevents the metal from adhering to the wall areas of the sample chamber.

It has also proven to be advantageous to cover the walls of the chamber bordering this gradation or strike surface with the wear-resistant layer in a width of about at least 5 mm.

For a sampling device with a one-piece sampling chamber, especially those wall areas which border the walls lying opposite the inlet pipe or its orifice and which run perpendicular to the direction of the inflowing metal should be covered with the wear-resistant layer in a width of about at least 5 mm.

For a sampling device with a chamber that has a wider width than height transverse to the direction of the inflowing metal, in the course of an extensive coating the walls with the wider width should preferably be completely coated.

A wear-resistant layer in the form of a ceramic layer is preferably applied. Especially good results were achieved with a ceramic layer in the form of an essentially oxide layer. It has been shown that, precisely with such an oxide layer, the metallic components of the sampling device are easily separated and the solidified sample easily removed. Oxide layers made of $Al_2O_3$ and $ZrO_2$ are preferably used. Above all, a layer made of $Al_2O_3$ is cheap and easy to apply, while a layer made of $ZrO_2$ is preferred when the temperature of the molten metal exceeds 1750° C.

These layers have the advantage that they only slightly influence the actual cooling off process of the metallic sample because they have good heat conductivity. In addition, they do not contain any binding agents or other materials that tend to gas formation or disintegration. Furthermore, it is possible to achieve a very thin and smooth surface with these layers.

Moreover, a layer made essentially of nitrides has proven to be advantageous as a wear-resistant layer, especially with molten metals having a higher temperature, since it enables the sampling device to be easily opened after the fluid metal has solidified. Such layers have the advantage that the surface achieved with them is very wear-resistant and, considering the tendency to pore formation, forms a very dense and closed surface. Plasma spraying and flame spraying have proven to be advantageous methods of applying the wear-resistant layers to the surfaces of the sampling chamber to be coated. It is possible to achieve a very smooth, thin layer especially by using plasma spraying. Applying a layer using flame spraying has proven to be advantageous when an inexpensive coating process is desired.

BRIEF DESCRIPTION OF THE DRAWINGS

The foregoing summary, as well as the following detailed description of presently preferred embodiments of the invention, will be better understood when read in conjunction with the appended drawings. It is understood, however, that this invention is not limited to the precise arrangements illustrated.

FIG. 1 is a front view of one component of a sampling device with two chamber areas;

FIG. 2 is a longitudinal crosssection taken along line II—II in FIG. 1;

FIG. 5 is a front view similar to FIG. 1 of one of the components of a sampling device which, however, has a single chamber with a uniform thickness; and FIG. 6 is a crosssection taken along line VI—VI in FIG. 5.

DETAILED DESCRIPTION OF THE PREFERRED EMBODIMENTS

Figure 3:
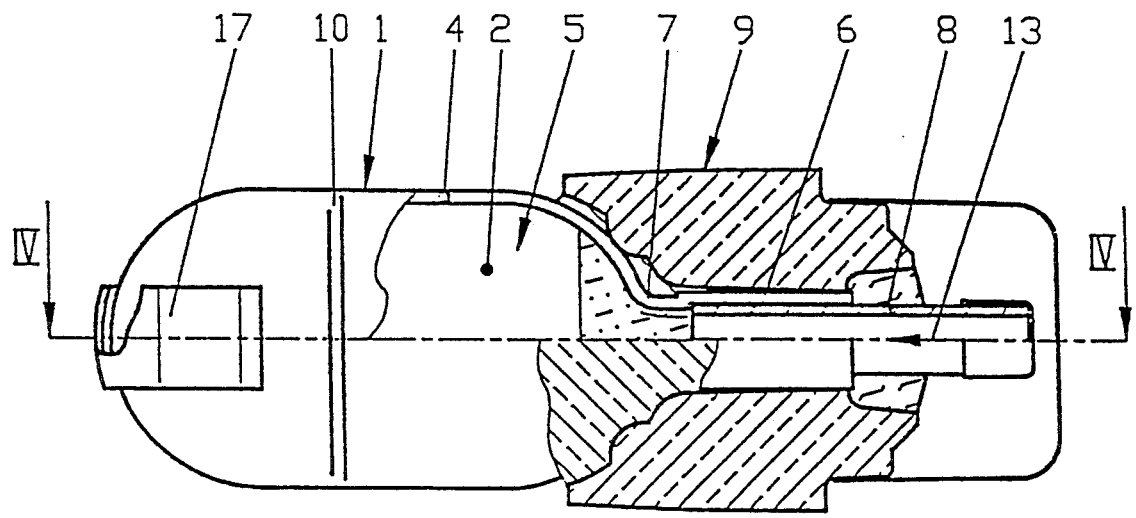
FIG. 3 is a partial sectional representation of the sampling device of FIG. 1 as it appears inserted in a measuring head.
Figure 4:
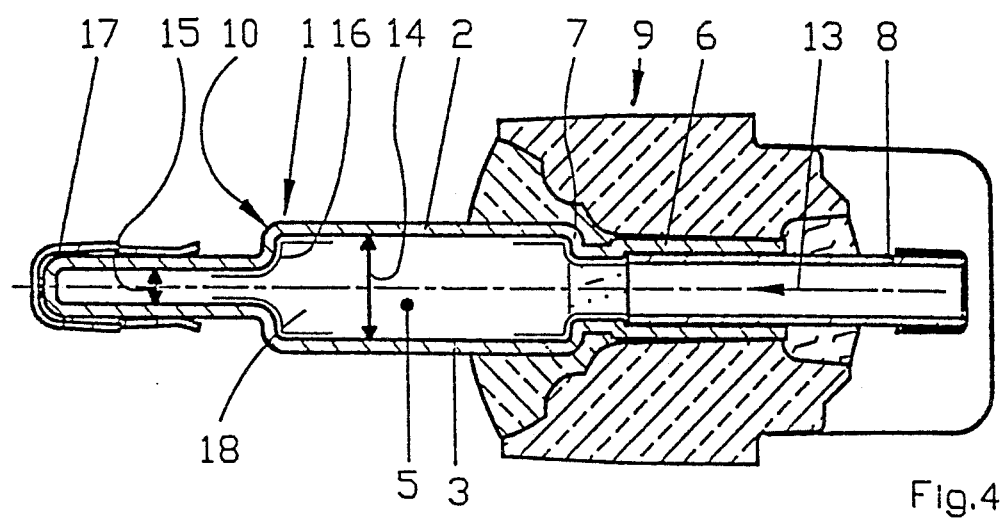
FIG. 4 is a crosssection taken along line IV—IV in FIG. 3.

The sampling device of FIGS. 1 and 2, as well as the sampling device 1 of FIGS. 3 and 4, has two identically constructed, cup-shaped, metallic components 2, 3, which lie with their front (mating) surfaces 4 facing each other and in this way enclose a chamber 5. In FIGS. 1 and 5 only one of each of the components 2, 3 of the sampling device is shown in a front view. FIGS. 3 and 4 show the complete sampling device 1 consisting of the two cup-shaped, metallic components 2,3 as it is inserted in the end of a measuring head 9. An inlet pipe 6 opens into this chamber 5, whereby this inlet pipe 6 is slightly narrowly constricted in the area of its orifice 7. The narrowing serves as an endstop for a small quartz pipe 8 which, as is shown in FIGS. 3 and 4, is inserted into the inlet pipe 6.

The sampling device of FIGS. 5 and 6 has a chamber 5 with a rounded outer contour and a uniform thickness in this rounded off area. In contrast, the sampling device of FIGS. 1, 2, 3 and 4 is subdivided by means of a gradation 10 into two chambers—areas 11,12. Viewed from the direction of the fluid metal streaming into the inlet pipe 6, whereby this direction of influx is indicated in the figures by the current arrow 13, the chamber area 11 with the wider width 14 lies closer to the orifice 7 of the inlet pipe 6, while the chamber area 12 with the smaller width 15 forms the end of the chamber 5. By means of a gradation 10, which extends at approximately right angles to the lateral walls of the sampling device 1, a strike surface 16 is created, upon which the fluid metal streaming into the sampling device 1 strikes. As is also shown in FIGS. 3 and 4, the components 2,3 of the sampling device 1 are held together by means of a spring clip 17.

The critical areas of the chamber 5 of the sampling device are coated with a wear-resistant layer 18. These critical areas are the area of the orifice 7 of the inlet pipe 6 in the chamber 5, as well as the opposite wall area 19 of the sampling device in FIGS. 5 and 6, i.e. that wall area which runs perpendicular to the direction of the current 13 of the fluid metal streaming into the chamber 5. These areas would exhibit the tendency for the fluid metal to adhere to the metallic components 2,3 if this wear-resistant layer 18 were not provided.

Viewed from the direction of the current 13, the width 20 of the wear-resistant layer 18 extends from the orifice 7 into half the length of the inlet pipe 6 and over a 5 mm wide area into the chamber 5. The chamber 5 is correspondingly coated with a layer in a width 20 of approximately 5 mm beginning from the wall area 19 in FIGS. 5 and 6. The coating is made of $Al_2O_3$ or $ZrO_2$ with a layer thickness 21 of approximately 60 micrometers.

For a sampling device with the chamber 5 subdivided into two chamber areas 11,12 it is essential, as FIGS. 1 and 2 indicate, that at least the strike surface 16 is coated with a wear-resistant layer 18 in the same way as the wall area 19 of the sampling device of FIGS. 5 and 6. In the area of this strike surface 16, viewed in the direction of the current 13 of the fluid metal, the ceramic layer is applied in a width 20 in such a manner that the coating begins at least about 5 mm in front of the strike surface and ends about 5 mm behind the strike surface. (Actually for this strike surface 16 it is a matter of two separate surfaces—that of component 2 and that of the other component 3.)

If it becomes necessary the entire chamber 5, i.e. the walls of the chamber area 11 with the widest width transverse to the direction of the current, can be coated with the wear-resistant layer 18. (Such an extensive coating is not shown in FIGS. 5 and 6 for the sampling device with the single chamber area.) Such an extensive ceramic layer 18 is certainly shown in the sampling device of FIGS. 1 and 2, whereby it was proven to be sufficient for such a sampling device with two chamber areas that only the chamber area 11 with the wide width 14 be coated. In this case, viewed from the direction of the current arrow, the coating also extends approximately 5 mm from the strike surface, 16 into the chamber area 12 with the smaller width 15.

In order to remove the solidified sample from the sampling device 1, as it is shown in FIGS. 3 and 4, the sampling device 1 is broken out of the measuring head 9, the spring clip 17 is released, and the two components 2,3 are separated from each other. By having the interior of the sampling chamber 5 coated with the wear-resistant layer 18, it is easy to separate the two components 2,3 from each other without having them adhere to the sample.

The present invention may be embodied in other specific forms without departing from the spirit or essential attributes thereof and, accordingly, reference should be made to the appended claims, rather than to the foregoing specification as indicating the scope of the invention.

I claim:

1. A sampling device for molten metal comprising at least two cup-shaped metallic components, each metallic component having a mating surface, each mating surface positioned to face the other mating surface to form a sampling chamber, and an inlet pipe opening into the sampling chamber, the inlet pipe having an orifice area, the sampling chamber having a wall area located opposite the orifice area, whereby at least the orifice area and the wall area have a wear-resistant layer which is temperature stable up to approximately 1700° C.

2. Sampling device according to claim 1, wherein the wear-resistant layer has a thickness of about 5 to 200 micrometers.

3. Sampling device according to claim 2, wherein the wear-resistant layer has a thickness of about 30 to 100 micrometers.

4. Sampling device according to claim 3, wherein the wear-resistant layer has a thickness of approximately 60 micrometers.

5. Sampling device according to claim 1, wherein the wear-resistant layer is a ceramic layer.

6. Sampling device according to claim 1, wherein the layer (18) is essentially an oxide layer.

7. Sampling device according to claim 6, wherein the oxide layer is $Al_2O_3$.

8. Sampling device according to claim 6, wherein the oxide layer is $ZrO_2$.

9. Sampling device according to claim 1, wherein the layer is essentially made of nitrides.

10. Sampling device according to claim 1, wherein the layer is applied by means of plasma spraying.

11. Sampling device according to claim 1, wherein the layer is applied by means of flame spraying.

12. A sampling device according to claim 1, wherein the wear-resistant layer extends from the orifice area of the inlet pipe to approximately 5 mm inside the sample chamber.

13. A sampling device according to claim 1, wherein the sampling chamber formed by the cup-shaped metallic components is subdivided into at least two chamber areas, each chamber area having a different width, the chamber areas positioned one behind the other in a direction generally parallel to the direction of the inlet pipe, the chamber areas being separated by a gradation in each component that forms a strike surface for molten metal which enters the sampling chamber through said orifice, at least one of the strike surfaces having a wear-resistant layer.

14. A sampling device according to claim 13, wherein the wear-resistant layer extends from the strike surface at least 5 mm into each chamber area.

15. A sampling device according to claim 1, wherein the chamber includes walls bordering the wall area located opposite the orifice area, the wear-resistant layer extending from the wall area to cover the walls of the chamber in a width of at least 5 mm.

16. A sampling device according to claim 1, wherein each chamber has a width, the chamber having the widest width having walls completely covered with the wear-resistant layer.

* * * * *